United States Patent [19]

Montgomery et al.

[11] Patent Number: 4,931,397

[45] Date of Patent: Jun. 5, 1990

[54] METHOD FOR REMOVING ANTIFOAMING AGENTS DURING PROCESSING OF MICROBIAL FERMENTATIONS

[75] Inventors: Curtis J. Montgomery, Elkhart; Chimanbhai P. Patel, Mishawaka; Jayarama K. Shetty, Elkhart, all of Ind.

[73] Assignee: Miles Inc., Elkhart, Ind.

[21] Appl. No.: 779,504

[22] Filed: Sep. 24, 1985

[51] Int. Cl.$^5$ .................. C12N 1/00; C12N 9/00; C12N 1/34

[52] U.S. Cl. .................. 435/243; 435/183; 435/246; 435/812; 435/814; 210/691; 252/321

[58] Field of Search .............. 435/243, 246, 803, 812, 435/814, 815, 816, 183, 261; 252/321; 502/407; 210/691; 203/20

[56] References Cited

U.S. PATENT DOCUMENTS

| | | | |
|---|---|---|---|
| 1,939,937 | 12/1933 | Werner | 252/321 X |
| 2,291,624 | 8/1942 | Heimann et al. | 502/407 X |
| 3,408,306 | 10/1968 | Boylan | 252/321 |
| 4,548,803 | 10/1985 | Dickey | 435/803 X |
| 4,657,859 | 4/1987 | Kelemen et al. | 435/803 X |

OTHER PUBLICATIONS

Zaborsky, Immobilized Enzymes, CRC Press, Cleveland, Ohio, 1973, pp. 75–81.

Peppler (editor), Microbial Technology, Reinhold Publishing, New York, 1967, pp. 375–377.

Hedman et al., "Enzyme Recovery by Adsorption From Unclarified Microbial Cell Homogenates", In: Enzyme Engineering 7, Laskin et al. (editor).

Annals of the New York Academy of Sciences, vol. 434, Dec. 31, 1984, pp. 285–288.

*Primary Examiner*—Randall E. Deck
*Attorney, Agent, or Firm*—Jennifer L. Skord

[57] ABSTRACT

Antifoaming agents are commonly used during culturing of enzyme-producing microorganisms. These antifoams often persist through enzyme processing, slowing filtrations, clogging filtration membranes and adversely affecting the quality of the final product. The present invention describes a method for removing antifoams, and often carbohydrates and pigments, from enzyme systems using mineral clay, the preferred clay being bentonite.

22 Claims, No Drawings

METHOD FOR REMOVING ANTIFOAMING AGENTS DURING PROCESSING OF MICROBIAL FERMENTATIONS

As foaming is a common problem during microbial production of enzymes, antifoaming agents are often employed. These antifoams, as well as other undesirable components such as carbohydrates and pigments, persist during enzyme processing and clog ultrafiltration membranes. The present invention contemplates the removal of antifoams, and often also carbohydrates and pigments, from an enzyme-containing whole fermentation broth or enzyme solution by the addition of mineral clay thereto.

BACKGROUND OF THE INVENTION

Foams, in this instance foamed fluids, are dispersions of air or other gas as the discontinuous phase in a continuous liquid phase. Usually since the air or gas makes up the larger volume of the foam, the foam bubbles are separated only by a thin liquid film. Unwanted fluid foams are made up of numerous tiny bubbles of a mechanical or chemical origin which are generated within a liquid and accumulate at the liquid surface faster than they decay. The formation of foams can be problematical during the culturing of microorganisms to produce enzymes. If not properly controlled, foam can reduce equipment capacity and increase processing time and expense as well as cause other difficulties, such as loss of biocatalytic activity. For these reasons, antifoaming agents, while being a necessity, are often undesirable or even detrimental when present in downstream processing steps or in the final product.

There are a wide variety of methods available to prepare antifoaming agents. See for instance, "Foam and Emulsion Control Agents and Processes", Colbert, J. C., Noyes Data Corporation, U.S.A., (1981). In the process described by J. B. Plumb, U.S. Pat. No. 3,865,859, Feb. 11, 1975, assigned to Imperial Chemical Industries Limited, England, silicone based polymers are prepared by reacting organochlorosilanes or alkoxysilanes with alkylene or oxyalkylene diols. These polymers, and many other silicone-based polymers, are very useful as surface active agents, particularly for suppression of foam formation in aqueous systems.

The present invention is particularly concerned with the extensive use of antifoams to control foam formation in the industrial production of enzymes. Since enzymes behave as biocatalysts, regulating many of the chemical reactions that naturally occur in living organisms, when isolated, enzymes have many such as in the tanning, detergent, and food industries. Typical industrial production involves incubating an enzyme-producing microorganism in an appropriate culture medium containing salt, a carbon source, a nitrogen source, and an antifoam. After the biomass is separated, the antifoam remains with the enzyme-containing solution, forming a slimy layer as it builds up on ultrafiltration membrane surfaces, greatly slowing the filtration.

It is well known that in general antifoams tend to form a precipitate as they become warmer. Thus, conventional enzyme processing often involves removal of antifoams by employing a heat step prior to ultrafiltration. For instance, the temperature of the entire enzyme solution is raised to 60° C. for several minutes or the enzyme solution is passed over heated coils to give a similar effect. The heating is followed by filtration to remove precipitated antifoam. This process is not only expensive in terms of energy usage, but is not feasible for heat-labile enzymes. In processing situations where heat treatment is not feasible or where heat treatment is not implemented until later stages of processing when the volume to be heated has been greatly reduced, enzyme solutions are kept cool to help the antifoam remain in solution and pass through filtration membranes. However, the great amount of friction occurring in the hollow-fiber membrane systems typically used in this step usually generates enough heat to cause the antifoam to precipitate and eventually clog the filtration membrane.

OBJECT AND ADVANTAGES OF THE INVENTION

The object of the present invention is to remove antifoaming agents from an enzyme-containing system. More particularly, this invention offers a simple and economical method involving the addition of a mineral clay, such as bentonite, to the enzyme whole broth or solution to remove antifoam, and often carbohydrates, and/or pigments.

SUMMARY OF THE INVENTION

The present invention provides an improved method of producing an enzyme by the culturing in a suitable nutrient growth medium of an enzyme producing microorganism to provide a fermentation broth which contains the enzyme wherein there is added to the fermentation broth a polycationic antifoaming agent. The improvement comprises (a) adding a mineral clay to the fermentation broth to form a complex with the antifoaming agent under pH conditions that will not result in the formation of a reaction product between the clay and enzyme so as to form a solid clay/antifoaming agent complex while leaving the enzyme in solution; and (b) separating the clay/antifoaming agent complex from the fermentation broth by solid/liquid separatory techniques. Also, the invention provides in combination with the method of producing an enzyme by the culturing in a suitable nutrient growth medium of an enzyme producing microorganism to provide a fermentation broth which contains the enzyme wherein there is added to the fermentation broth a polycationic antifoaming agent, the improvement which comprises: (a) adding a mineral clay to the fermentation broth to form a complex with the antifoaming agent under pH conditions that will result in the formation of a reaction product between the clay and enzyme so as to form both a solid clay/antifoaming agent complex and an insoluble enzyme/clay reaction product; (b) adjusting the pH to outside the range in which the enzyme and clay form a reaction product whereby the enzyme goes into solution; and (c) separating the clay/antifoaming agent complex from the fermentation broth by solid/liquid separatory techniques. Also, the method may be employed with a cell-free filtrate or supernatant after removal of biomass from the whole fermentation broth.

DETAILED DESCRIPTION OF THE INVENTION

The present invention works well for both intracellular and extracellular enzymes or a mixture thereof. Thus, the enzyme may be an extracellular type that is secreted during a fermentation, or the enzyme may be an intracellular type that is solubilized by well known methods, for instance sonication or the addition of a detergent to disrupt the cell and thereby render the enzyme outside the cell. Some microorganisms produce both kinds of enzymes under appropriate conditions.

The clay may be added directly to the whole fermentation broth. By fermentation broth, it is meant all the products present immediately after fermentation, such as the enzyme(s), the biomass and the residual fermentation nutrients from the enzyme production process.

After the clay is added, it forms a complex with the antifoaming agent remaining from the enzyme production process while leaving the enzyme in solution. This complex coagulates and settles to the bottom of the reaction vessel. Thus, when the biomass is separated from the broth, the clay/antifoaming agent complex will also be removed. After addition of the clay, any solid/liquid separatory technique, such as filtration or centrifugation followed by decantation, can be used to separate the complex from the fermentation broth.

The present invention also contemplates separating the biomass from the enzyme-containing fermentation broth before the addition of the particulate clay. Any solid/liquid separatory technique such as filtration or centrifugation may be used to remove the biomass thereby providing a cell-free enzyme-containing solution. Then, the clay may be added to the enzyme-containing solution, i.e. the culture filtrate or supernatant, to form a clay/antifoaming agent complex, which can be separated from the liquid by any solid/liquid separatory technique.

In another embodiment, the biomass may be reslurried, for instance in aqueous solution, the slurry centrifuged or filtered to separate the biomass, and then additional clay added to the second supernatant or filtrate. This will raise the final enzyme yield by "rinsing" the cells in the biomass to collect residual enzyme. Just as when the process is carried out employing the whole fermentation broth, a clay/residual antifoaming agent complex will form. The complex coagulates and can be separated, such as by filtration or centrifugation. Additional enzyme is thereby recovered.

It is noted that with the embodiments involving adding clay to the whole fermentation broth, over 10% of the antifoam can be separated together with the biomass. On the other hand, when the fermentation broth is first treated, such as by filteration or centrifugation to remove or separate the biomass, substantially all the antifoam, i.e. 90% or more, can be separated. Accordingly, it is preferred that the fermentation broth be treated to provide a cell-free enzyme-containing solution before addition of the clay.

Enzyme fermentations often contain carbohydrate materials such as sugars or starches (which increase the viscosity of the fermentation broth during enzyme processing) and pigments (which impart undesirable color to the final product). These are often also capable of forming a complex with the clay and can thus be separated and removed together with the antifoam, by any solid/liquid separatory technique. For instance, the removal of carbohydrate after culturing a strain of Bacillus licheniformis to produce alkaline protease is illustrated in Example I below.

It should be noted that the formation of the clay/antifoaming agent complex is not pH dependent. Thus, if the invention is practiced with enzymes of the type that are immobilized on clay, then in one embodiment the addition of the clay may be under pH conditions that will not result in the formation of a reaction product between the clay and enzyme. For instance, at an appropriate pH, clay will immobilize certain enzymes by the formation of an insoluble reaction product therebetween. Such an enzyme is transglucosidase, and its immobilization on clay at pH 3-5 is disclosed in U.S. Pat. No. 3,042,584. Also, it is disclosed in U.S. Pat. No. 3,899,395 that bentonite will form an insoluble reaction product with lipase at a pH of from 4-6. Accordingly, the clay may be added under pH conditions which will not form a reaction product between the clay and the enzyme. In the other embodiment with enzymes of the type that are immobilized on clay, the addition of the clay may be under pH conditions that will result in the formation of an insoluble enzyme/clay reaction product. It will settle to the bottom of the reaction vessel together with the clay/antifoaming agent complex. Then the pH can be adjusted outside the range in which the enzyme and clay form a reaction product. This will cause the enzyme to leave the clay and go back into solution. The solid clay/antifoaming agent complex can then be separated by any solid/liquid separatory technique as described above. Of course, if the enzyme(s) are of the type that form little or no reaction product with clay, then the addition of clay may be at any pH as long as the pH is selected so as not to affect the activity of the enzyme(s) to an undesirable extent. The pH can be readily determined by the person skilled in the art in accordance with the pH sensitivity of the particular enzyme or enzymes as further discussed below.

The affinity between the clay and the antifoam is believed to be a surface effect and thus it is possible to conduct the present process simply by passing a fermentation broth or enzyme-containing solution over a clump of clay. However, as the surface area of the clay increases, the clay will be more effective in removing antifoam. Thus, the clay should be in the particulate form. In a desired embodiment, the particle size of the clay is such that approximately 60% to 80% of the clay will pass through a sieve having a U.S. mesh size ranging from approximately 140 mesh (106 micrometers) to 230 mesh (63 micrometers). Although there is no required minimum particle size, it is preferred that substantially all the particles are retained by a sieve of approximately 270 mesh (53 micrometers).

Any mineral clay can be used in accordance with the invention. Preferred are hydrated alumina silicates such as monomorillonite, bentonite, attapulgite, illite, and kaolin. A particularly suitable clay is Volclay ® which is a western bentonite commercially available from American Colloid Company of Skokie, Ill. A technical description of it is as follows:

| VOLCLAY ® | |
|---|---|
| GENERAL DESCRIPTION: | A high yield Wyoming bentonite to be used where high viscosity slurries are required - typically in slurry trenches. |
| APPEARANCE: | A light buff powder. |
| COMPOSITION: | Consists mainly of montmorillonite, with traces of quartz, gypsum, etc. |
| PHYSICAL CHARACTERISTICS: | Moisture 10% maximum. Fineness minimum 70% passing 200 mesh (75 micrometers). pH 8 to 10 in 1% suspension. Bulk density 67 lbs. per cubic foot. |
| YIELD: | Minimum 180 barrels (42 gal.) of suitable viscosity slurry per 2000 lbs. of Volclay ®. |
| HANDLING PRECAUTIONS: | No special hazards. Breathing of dust may cause dryness of nose |

| | VOLCLAY ® |
|---|---|
| | and throat. |
| PACKAGING: | 100 lb. and 50 lb. multiwall paper bags and bulk. |

The clay should be added to a final amount from approximately 0.01% to 10%, more preferably approximately 0.1% to 5%, and even more preferably approximately 1.5% to 3%, weight of clay to volume of fermentation broth or cell free enzyme-containing solution. In general, it is not necessary to add the clay in any particular manner, or at any particular temperature. However, it is preferred to add the clay slowly in small increments with substantially uniform stirring until the desired concentration is reached. Stirring is desirably continued to provide a uniform dispersion. Also, the temperature is preferably maintained at approximately 5° C. to 35° C. In general, a temperature of approximately 19° C. to 28° C. may be employed, but of course stirring in the cold is advantageous in helping to ensure that the antifoam does not precipitate on its own prior to forming the clay/antifoam complex. It is desirable to continue the stirring for up to 3 hours to ensure adequate contact of the clay with the antifoam and other components such as pigments and carbohydrates. For instance, in a preferred embodiment, after the addition of the clay, the stirring is continued for 45 minutes at 5° C. to allow the antifoam, pigment and/or carbohydrate to come into contact with the clay.

Also, depending on the particular enzyme, the pH may be adjusted to help maintain enzyme activity. It is well known in enzyme processing that activity may be affected by pH. Agents for adjustment are well known and are chosen in accordance with the particular enzyme. Typical agents are bases such as KOH and NaOH, and acids such as hydrochloric and acetic. It is also noted that the pH may already be at an adequate level due to pH agents typically used during culturing of microorganisms. Thus, the pH should be selected so that it does not affect the enzyme's activity to an undesirable extent. The pH at which to operate will depend on the pH sensitivity of the particular enzyme involved, but can readily be determined by the person skilled in the art without undue experimentation.

The antifoaming agent may be chosen from the silicone-based polymer emulsion antifoams. Suitable ones are the MAZU ® antifoams supplied by Mazer Chemicals Inc. of Gurnee, Ill., and the SAG ® and SENTRY ® antifoams supplied by Union Carbide of Danbury, Conn.

The antifoaming agent used in the examples was MAZU DF 6000, a polypropylene glycol-silicone (PPGS) emulsion of molecular weight 2000-6000. The detection method chosen for this antifoam was the nephelometric determination of PPGS. The determination of PPGS is based on the formation of a measurable precipitate when PPGS complexes with potassium iodomercurate, described by the following chemical formula:

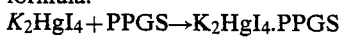
$K_2HgI_4 + PPGS \rightarrow K_2HgI_4 \cdot PPGS$

Because PPGS displays an inverse relationship between solubility and temperature and has its cloud point (the sudden onset of turbidity of a nonionic solution on raising the temperature) close to room temperature, samples are heated to improve sensitivity and reproducibility. The procedure is described in M. Musho, *Analytical Research Procedure,* number I-2-1-16.0.

The clay and the antifoam have an affinity for each other. The exact mechanism is not known, but it is postulated that antifoams, which are generally polycationic, are electrostatically held by the clay particles, which are generally anionic, resulting in a complex which precipitates and is easily separated by any solid/liquid separatory technique, such as filtration, from a whole fermentation broth together with the biomass, or alternatively, separated from an enzyme-containing solution which has already been treated to remove the biomass.

The phenol-sulfuric acid method was used to determine total carbohydrate (Montgomery, R., 1961, Biochem., Biophys. Acta, 48, 591).

The total protein was determined by using the Bio-Rad Protein Assay dye method as described in Publication No. 84-0047/284, by Bio-Rad Laboratories of Richmond, Calif. which is a rapid protein measurement. It is a dye-binding assay based on the differential color change of a dye in response to various concentrations of protein based on the method of Bradford, *Anal. Biochem.* vol. 72, page 248 (1976). In a typical assay 0.1 ml properly diluted sample is mixed with 5.0 ml dye reagent. A blue-green color results which is read by spectrophotometer at 595 nm. A standard curve was prepared using 10-150 micrograms gamma globulin.

It is noted that where color (pigment) was tested in the Examples below, the absorbance of the appropriately diluted sample was measured at 400 nm in a spectrophotometer.

The invention will work with any enzyme. The Examples below employ enzyme(s) from *Bacillus licheniformis* and *B. amyloliquefaciens*.

A fermentation to produce bacterial alkaline protease (AP) from a strain of *Bacillus licheniformis* can be conducted by adding soy media, salt(s), starch(es), alpha amylase (to aid in hydrolyzing the starch(es) to soluble dextrins), antifoam, and water to a fermentor, and then inoculating this medium with viable cells of a strain of *B. licheniformis*. The fermentation is allowed to continue for 1 to 2 days at 35°-40° C. Next, the whole broth is usually diluted with water and the pH may be adjusted to slightly basic. A suitable flocculant may be added to aid in flocculating biomass.

A fermentation to produce thermally stable bacterial alpha-amylase (AA) from a strain of *Bacillus licheniformis* can be conducted by adding soy meal, cotton seed meal, salt(s), sugar(s), antifoam, and water to a fermentor, and then inoculating this medium with viable cells of a strain of *Bacillus. licheniformis*. The fermentation is allowed to continue for 3 to 4 days at 40°-45° C. while maintaining the pH around neutral. A suitable flocculant may be added to the whole fermentation broth to aid in flocculating the biomass.

A fermentation to produce bacterial neutral protease (NP) from a strain of *Bacillus amyloliquefaciens* can be conducted by adding a suitable nitrogen source, salt(s), carbohydate(s), antifoam, and water to a fermentor, and then inoculating this medium with viable cells of a strain of *Bacillus. amyloliquefaciens*. The fermentation is allowed to continue for 2 to 4 days at 25° C. to 35° C. while maintaining the pH at between 5.5 and 7.5. A suitable flocculant may be added to the whole fermentation broth to aid in flocculating biomass. It is noted this fermentation also produces significant levels of alpha-amylase, beta-glucanase, hemicellulase, and cellulase.

The following Examples are intended to illustrate the preferred embodiments of the invention, and it is not intended to limit the claims thereby.

EXAMPLE I

A fermentation broth containing alkaline protease from *B. licheniformis* prepared as described above was filtered to remove biomass thereby providing cell-free culture filtrate. Various aliquots of 200 ml each from the culture filtrate were adjusted to pH 7.7, 8.5, 9.0 and 9.5, respectively, using aqueous 10% w/v (weight/volume) KOH. An aliquot (at pH 7.7) was kept as a control and Volclay ® bentonite was added in small increments with constant stirring to the other aliquots to a final concentration of 2% w/v. The suspensions were stirred for 45 minutes at 5° C. The cold ensured that the antifoam did not precipitate on its own, but rather stayed in solution so that contact with the clay formed a clay-antifoam complex. The flocculated complex was separated by filtration. The resultant filtrates were analyzed for antifoam content, total carbohydrate, and enzyme activity. The results show bentonite to be effective in removing antifoam and carbohydrate from the culture filtrate with only slight loss of enzyme activity, and are reported in Table I below. Activity was determined using the method described in Miles Laboratories, Inc., Biotechnology Quality Assurance Procedure No. 400.23 which is based on the Delft Assay method as developed by the Royal Netherlands Fermentation Industries, Ltd., Delft, Holland. Activity is reported in alkaline protease units per milliliter. Carbohydrate is reported in milligrams per millimeter, and antifoam is reported in parts per million.

TABLE I

| Sample (percent bentonite in w/v) | pH | Antifoam (ppm) | Carbohydrate (mg/ml) | Enzyme Activity (APU/ml) |
|---|---|---|---|---|
| 1. AP + 0% | 7.7 | 1000 | 25 | 8440 |
| 2. AP + 2% | 7.7 | 30 | 15 | 7700 |
| 3. AP + 2% | 8.5 | 36 | — | 7700 |
| 4. AP + 2% | 9.0 | 40 | — | 7700 |
| 5. AP + 2% | 9.5 | 53 | — | 7700 |

EXAMPLE II

The procedure of Example I was repeated for an alkaline protease culture filtrate, except the optimum level of bentonite to be added to the culture filtrate for removal of antifoam was determined by mixing 200 ml aliquots of culture filtrate with 0.5% to 3% w/v Volclay ® bentonite at pH 7.5. The results are depicted in the Table below.

TABLE II

Effect of bentonite concentration on the removal of antifoaming agent from alkaline protease culture filtrate derived from *Bacillus licheniformis* at pH 7.5, 25° C.

| Bentonite Concentration (g/100 ml) | Percent Antifoam Remaining |
|---|---|
| Control, 0 | 100 |
| 0.5 | 26 |
| 1.0 | 23 |
| 1.5 | 8 |
| 2.0 | 4 |
| 2.5 | 3 |
| 3.0 | 3 |

Table II illustrates that increasing levels of betonite remove antifoam. The optimum level appears to be 1.5–3% w/v bentonite since at the 1.5% w/v level of bentonite, the level of antifoam remaining in the culture filtrate is reduced to less than 10%, whereas after the addition of 3.0% w/v bentonite the antifoam remaining is only 3%.

EXAMPLE III

A whole fermentation broth containing alpha amylase produced by *B. licheniformis* as described above was first filtered to remove biomass and provide cell-free culture filtrate for this Example. Two whole broths were also treated. To aliquots of 100 ml each from the thermostable alpha-amylase fermentation culture filtrate was added Volclay ® bentonite in the same manner as in Example I in a concentration of 2 and 3% w/v to determine the effect on antifoam and carbohydrate, and to one of the whole broth samples was added 3% w/v Volclay ® bentonite. Control samples (no bentonite) of the whole broth and of the culture filtrate (CF) were also tested at pH 7.5. Antofoam and carbohydrate content were measured in the same manner as in Example I. The samples were also tested in a colorimeter for the presence of pigments. Total protein was checked using the Bio-Rad method described above, and is reported in mg/ml. The results are summarized in Table III below.

TABLE III

| Treatment | Antifoam (micrograms PPGS) | Carbohydrate (mg/ml) | Total Protein (mg/ml) | Color (400 nm) |
|---|---|---|---|---|
| 1. Whole broth control | 32,500 | 5.6 | 10.4 | 0.421 |
| 2. 3% bentonite to whole broth | 28,200 | 7.8 | 11.0 | 0.300 |
| 3. CF control | 11,500 | 7.5 | 11.0 | 0.290 |
| 4. 2% bentonite to CF | 3,500 | 7.8 | 11.0 | 0.270 |
| 5. 3% bentonite to CF | 750 | 7.5 | 9.8 | 0.250 |

The bentonite is very effective in removing the antifoam from AA culture filtrate just as with AP culture filtrate. Also, the bentonite effectively removed some of the undesirable colorants. However, the bentonite appears to be ineffective in removing residual carbohydrate from the AA culture filtrate as compared to removing residual carbohydrate from the AP culture filtrate as in Example I.

With regard to the whole broth, the bentonite removed over 13% of the antifoam, and some color, but appears to be ineffective in removing carbohydrate.

EXAMPLE IV

An alpha amylase producing fermentation of *B. licheniformis* as described above was conducted to provide a whole broth for this Example. Instead of filtering, the alpha-amylase containing liquid was separated from the biomass by centrifugation, followed by decantation of the supernatant. The removal of antifoam by adding 2% w/v Volclay ® bentonite to the supernatant was studied again using the same procedure as in Example III. It was found that 20% of the antifoam was in the supernatant, and thus 80% of the antifoam had remained with the biomass after the centrifugation of the whole broth. Next, the biomass was resuspended in water to the original volume of the whole broth and then centrifuged, followed by decantation of the supernatant to extract residual enzyme. This second supernatant was treated in the same manner with 2% w/v Volclay ® bentonite, and it was found that most of the residual antifoam was also extracted from the biomass into this second decanted supernatant.

The bentonite treatment of the first supernatant removed more than 90% of the remaining antifoam, resulting in an enzyme liquid with only 15 ppm PPGS. The bentonite treatment of the second supernatant removed most of the residual antifoam, resulting in an enzyme liquid with only 25 ppm PPGS.

EXAMPLE V

A whole fermentation broth for bacterial neutral protease from *Bacillus amyloliquefaciens* prepared as described above also containing a high level of alpha-amylase and significant levels of beta-glucanase, hemicellulase, and cellulase activities was tested. After separation of the biomass by filtration, 50 ml aliquots of the primary filtrate were treated with various levels of Volclay ® bentonite at a pH of 6.2 and also at different pH's with 0.5% w/v bentonite. The pH was adjusted with aqueous 10% w/v KOH. Addition of the bentonite was conducted as in Example I. The effectiveness of antifoam removal was measured in the same manner as in Example I. The samples having a pH 6.2 were also tested in a colorimeter. The results are reported in Table V below.

TABLE V

| Run No. | Bentonite Level | pH | Antifoam PPGS(ppm) | Percent Antifoam Removed | Color (400 nm) |
|---|---|---|---|---|---|
| 1. | 0% | 6.2 | 51,000 | 0 | 0.475 (× 10) |
| 2. | 0.1% | 6.2 | 48,000 | 5.9 | 0.447 (× 10) |
| 3. | 0.5% | 6.2 | 35,200 | 31.0 | 0.436 (× 10) |
| 4. | 1.0% | 6.2 | 30,000 | 41.2 | 0.436 (× 10) |
| 5. | 1.5 | 6.2 | 5,500 | 89.2 | 0.370 (× 10) |
| 6. | 2.0% | 6.2 | 2,100 | 95.9 | 0.368 (× 10) |
| 7. | 3.0% | 6.2 | 1,200 | 97.7 | 0.339 (× 10) |
| 8. | 0.5% | 5.0 | 28,800 | 45.6 | N/A* |
| 9. | 0.5% | 6.0 | 28,800 | 45.6 | N/A |
| 10. | 0.5% | 7.0 | 24,000 | 52.9 | N/A |
| 11. | 0.5% | 8.0 | 21,250 | 58.5 | N/A |
| 12. | 0.5% | 9.0 | 21,250 | 58.5 | N/A |

*Not available

For neutral protease at an acid pH of 6.2, the bentonite is most effective at concentrations of at least 1.5% w/v bentonite (aliquots 5, 6 and 7), whereas at a low level of 0.5% w/v bentonite the removal of antifoam clearly improves at an alkaline pH (aliquots 8-12).

EXAMPLE VI

Ultrafiltration studies using an Amicon ® 76 mm disc PM-10 membrane, supplied by Rohm and Haas, showed a nearly 3-fold increase in flow rate, volume/time, as measured by the amount of permeate collected in 1 hour for the 1.5% w/v Volclay ® bentonite treated neutral protease filtrate as described in Example V as compared to a control protease filtrate. The results are summarized in Table VI below.

TABLE VI

|  | 1.5% w/v Bentonite | Control (No Bentonite) |
|---|---|---|
| Start Volume | 500 ml | 500 ml |
| pH | 6.2 | 6.2 |
| Temperature | 5° C. | 5° C. |
| Stirring | 300 RPM | 300 RPM |
| Pressure | 40 psi (3.845 kg/cm$^2$) | 40 psi (3.845 kg/cm$^2$) |
| Permeate Volume collected after 1 Hour | 24 ml | 70 ml |

We claim:

1. In combination with the method of producing an enzyme by the culturing in suitable nutrient growth medium of an enzyme producing microorganism to provide a fermentation broth which contains the enzyme wherein there is added to the fermentation broth a polycationic antifoaming agent, the improvement which comprises:
   (a) adding a mineral clay to the fermentation broth after separating biomass therefrom and adjusting the pH to a level at which the clay will not form a complex with the enzyme to form a solid clay/antifoaming agent complex while leaving the enzyme in solution; and
   (b) separating the clay/antifoaming agent complex from the fermentation broth by solid/liquid separatory techniques.

2. The method of claim 1, wherein in (a) the clay is added with substantially uniform stirring and the stirring is continued for up to 3 hours and wherein in (b) said separation is accomplished by filtration or centrifugation followed by decantation.

3. The method of claim 2, wherein the clay is a montmorillonite, a hydrated alumina silicate, an attapulgite, an illite, a kaolin, or a mixture thereof, and the clay is added in the amount of approximately 0.01% to 10% weight to volume of enzyme-containing solution.

4. The method of claim 3, wherein the clay has a particle size such that approximately 60% to 80% of the clay will pass through a sieve having a U.S. mesh size ranging from approximately 140 mesh to 230 mesh.

5. The method of claim 4, wherein the antifoaming agent is a silicone based polymer emulsion.

6. The method of claim 5, wherein the antifoaming agent is a polypropylene glycol-silicone emulsion with a molecular weight range of 2000-6000.

7. The method of claim 1, wherein the enzyme is secreted by the microorganism and is therefore extracellular.

8. The method of claim 1, wherein the enzyme is initially intracellular and is solubilized whereby it is rendered outside the cell walls of the enzyme-producing microorganism.

9. The method of claim 1, wherein the clay is a montmorillonite, a hydrated alumina silicate, an attapulgite, an illite, a kaolin, or a mixture thereof, and the clay is added in the amount of approximately 1.0% to 10% weight to volume of enzyme-containing solution.

10. The method of claim 9, wherein the clay has a particle size such that approximately 60% to 80% of the clay will pass through a sieve having a U.S. mesh size ranging from approximately 140 mesh to 230 mesh.

11. The method of claim 10, wherein the antifoaming agent is a silicone based polymer emulsion.

12. The method of claim 11, wherein the antifoaming agent is a polypropylene glycol-silicone emulsion with a molecular weight range of 2000-6000.

13. The method of claim 12, wherein the enzyme is secreted by the microorganism and is therefore extracellular.

14. The method of claim 12, wherein the enzyme is initially intracellular and is solubilized whereby it is rendered outside the cell walls of the enzyme producing microorganism.

15. The method of claim 1, further including recovering additional enzyme by (c) reslurrying the separated biomass in aqueous solution, (d) reseparating the biomass to provide a solution of residual enzyme, (e) adding additional mineral clay to the solution of residual enzyme so as to form a solid clay/residual antifoaming agent complex, and (f) separating the clay/residual antifoaming agent complex from the solution.

16. The method of claim 15, wherein in (a) the clay is added with substantially uniform stirring and the stirring is continued for up to 3 hours and wherein in (b) said separation is accomplished by filtration or centrifugation followed by decantation.

17. The method of claim 16, wherein the clay is a montmorillonite, a hydrated alumina silicate, an attapulgite, an illite, a kaolin, or a mixture thereof, and the clay is added in the amount of approximately 0.01% to 10% weight to volume of broth.

18. The method of claim 17, wherein the clay has a particle size such that approximately 60% to 80% of the clay will pass through a sieve having a U.S. mesh size ranging from approximately 150 mesh to 230 mesh.

19. The method of claim 18, wherein the antifoaming agent is a silicone based polymer emulsion.

20. The method of claim 19, wherein the antifoaming agent is a polypropylene glycol-silicone emulsion with a molecular weight range of 2000–6000.

21. The method of claim 20, wherein the enzyme is secreted by the microorganism and is therefore extracellular.

22. The method of claim 20, wherein the enzyme is initially intracellular and is solubilized whereby it is rendered outside the cell walls of the enzyme producing microorganism.

* * * * *

UNITED STATES PATENT AND TRADEMARK OFFICE
CERTIFICATE OF CORRECTION

PATENT NO. : 4,931,397
DATED : June 5, 1990
INVENTOR(S) : Curtis J. Montgomery et al It is certified that error appears in the above-identified patent and that said Letters Patent is hereby corrected as shown below:

At column 1, line 52 "have many such as" should be ---have, many uses, such as--.

At column 3, line 1 "disrupt the cell" should be ---disrupt the cells---.

At column 8, line 22 "Antofoam" should be ---Antifoam---.

At column 10, line 58 "1.0% to 10%" should be ---0.1% to 10%---.

Signed and Sealed this

Sixth Day of August, 1991

*Attest:*

HARRY F. MANBECK, JR.

*Attesting Officer*      *Commissioner of Patents and Trademarks*